US006294356B1

(12) United States Patent
Jones et al.

(10) Patent No.: US 6,294,356 B1
(45) Date of Patent: Sep. 25, 2001

(54) METHODS AND MATERIALS FOR MAKING AND USING LAMININ-5

(75) Inventors: Jonathan C. R. Jones; M. Sharon Stack, both of Chicago; Lawrence E. Goldfinger, Evanston, all of IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 09/232,394

(22) Filed: Jan. 15, 1999

Related U.S. Application Data
(60) Provisional application No. 60/071,663, filed on Jan. 16, 1998.

(51) Int. Cl.[7] ............................... C12P 21/06; C12P 21/02
(52) U.S. Cl. ..................... 435/69.1; 435/68.1; 530/350; 530/395
(58) Field of Search ........................ 530/350, 395; 435/68.1, 69.1

(56) References Cited

U.S. PATENT DOCUMENTS

| | | | |
|---|---|---|---|
| 5,026,637 | 6/1991 | Soule et al. | 435/29 |
| 5,206,165 | 4/1993 | Pauley et al. | 435/240 |
| 5,238,840 | 8/1993 | Pauley et al. | 435/240 |
| 5,352,668 | 10/1994 | Burgeson et al. | 514/21 |
| 5,422,264 | 6/1995 | Quaranta et al. | 535/240 |
| 5,436,152 | 7/1995 | Soule et al. | 435/240 |
| 5,510,263 | 4/1996 | Quaranta et al. | 435/240 |
| 5,541,106 * | 7/1996 | Jones | 435/240.243 |
| 5,658,789 * | 8/1997 | Quaranta et al. | 435/375 |
| 5,660,982 | 8/1997 | Tryggvason et al. | 435/6 |
| 5,672,361 | 9/1997 | Halberstadt et al. | 424/556 |
| 5,681,587 | 10/1997 | Halberstadt et al. | 424/562 |
| 5,760,179 | 6/1998 | Fitchmun | 530/350 |
| 5,770,448 * | 6/1998 | Jones et al. | 435/325 |

FOREIGN PATENT DOCUMENTS

| | | |
|---|---|---|
| WO 92/17498 | 10/1992 | (WO) . |
| WO 94/05316 | 3/1994 | (WO) . |
| WO 95/06660 | 3/1995 | (WO) . |
| WO 97/36621 | 10/1997 | (WO) . |
| WO 97/48415 | 12/1997 | (WO) . |

OTHER PUBLICATIONS

Baker, Exp. Cell Res., 228:262–270 (1996).
Baker et al., J. Cell Sci., 109:2509–2520 (1996).
Bergstraesser et al., American Journal of Pathology, 147(6):1823–1839 (1995).
Carter, et al., Cell, 65:559–610 (1991).
Champliaud et al., J. Cell Biol., 132:1189–1198 (1997).
Chapman, British Journal Dermatology, 123:137–144 (1990).
Giudice, et al., "Cloning and Primary Structural Analysis of the Bullous Pemphigoid Autoantigen BP180," The Society of Investigative Dermatology, Inc., 99(3):243–250 (1992).
Guidice et al., J. Clin. Invest., 87:734–738 (1991).
Goldfinger et al., J. Cell Biol., 141:255–265 (1998).
Hieda, et al., J. Cell Biol., 116(6):1497–1506 (1992).
Hopkinson et al., J. Invest. Dermatol., 99(3):264–70 (1992).
Hormia et al., J. Invest. Dermatol., 105:557–561 (1995).
Hsi, et al., Placenta, 8:209–217 (1987).
Jones, et al., Cell Regulation, 2:427–438 (1991).
Jones, et al., Exp. Cell Res., 213:1–11 (1994).
Jones et al., Current Opinion in Cell Biology, 3:127–132 (1991).
Kallunki et al., J. Cell Biol., 119:679–693 (1992).
Kurpakus, et al., J. Cell Biol, 115(6):1737–1750 (1991).
Langhofer, et al., J. Cell Science, 105:753–764 (1993).
Malinda et al., Int. J. Biochem Cell Biol., 28:957–959 (1996).
Marinkovich et al., J. Biol Chem., 267:17900–17906 (1992).
Matusi et al., J. Invest. Derm., 105:648–652 (1995).
Matusi et al., J. Biol Chem., 270:23496–23503 (1995).
O'Toole et al., Exp. Cell Res., 233:330–339 (1997).
Pyke et al., Am J. Pathol., 145:782–791 (1994).
Pyke et al., Cancer Res., 55:132–4139 (1995).
Plopper et al., J. Cell Science, 109:1965–1973 (1996).
Riddelle et al., J. Cell Science, 103:475–490 (1992).
Riddelle, et al., J. Cell Biol., 112(1):159–168 (1991).
Roskelly et al., Curr. Op. Cell Biol.m 7:736–747 (1995).
Rouselle, et al., J. Cell Biol., 114(3):567–576 (1991).
Sonnenberg, et al., J. Cell Biol., 113(4):907–917 (1991).
Soule, et al., Cancer Research, 50:6075–6086 (1990).
Staehelin, International Review of Cytology, 39:191–283 (1974).
Stahl et al., J. Cell Sci., 110:55–63 (1997).
Stepp, et al., Proc. Natl. Acad. Sci. USA, 87:8970–8974 (1990).
Streuli et al., J. Cell Biol., 129:591–603 (1993).
Tait, et al., Cancer Research, 50:6087–6094 (1990).
Timpl et al., Matrix Biol., 14:275–281 (1994).
Tryggvason, Curr, Op. Cell Biol., 5:877–882 (1993).
Vailly et al., Eur. J. Biochem., 219:209–218 (1994).
Verrando, et al., Biochim. Biophys. Acta., 942:45–56 (1988).
Yurchenco et al., Proc. Nat'l Acad. Sci., 94:10189–10194 (1997).
Zackroff et al., J. Cell Biol., 98:1231–1237 (1984).
Zhang and Kramer, Exp. Cell Res., 227:309–333 (1996).

* cited by examiner

Primary Examiner—Karen Cochrane Carlson
Assistant Examiner—Stephen Tu
(74) Attorney, Agent, or Firm—Sheridan Ross P.C.

(57) ABSTRACT

The invention provides two forms of laminin-5. One form comprising unprocessed α3 subunits promotes the migration of epithelial cells. The other form comprising plasmin-cleaved α3 subunits promotes the formation of hemidesmosomes. The invention further provides methods of making and using the two forms of laminin-5 and products comprising the two forms of laminin-5.

14 Claims, No Drawings

METHODS AND MATERIALS FOR MAKING AND USING LAMININ-5

Benefit of provisional application number 60/071,663, filed Jan. 16, 1998, is hereby claimed.

This work was supported by National Institutes Of Health (NIH) grants GM38470 and CA58900, NIDR grant DE12328, and U.S. Army grant DAMD17-94-J-4291. The government has certain rights in the invention.

FIELD OF THE INVENTION

This invention relates to two forms of laminin-5. One of these forms promotes the migration of epithelial cells. The other form promotes hemidesmosome assembly. The invention also relates to methods of making and using the two forms of laminin-5 and to products comprising them.

BACKGROUND

Epithelial cells are separated from connective tissue by a basement membrane, which is composed of a variety of extracellular matrix molecules, including proteoglycans, collagen and laminin isoforms. Together these proteins create a framework that is essential for maintaining tissue integrity. However, extracellular matrix proteins play more than just a structural role. They also display a diverse set of biological functions that regulate adhesion, migration, proliferation, differentiation and gene expression of adjacent cells. Roskelly, et al., *Curr. Op. Cell Biol.* 7:736–747 (1995).

Laminin, of which there are at least ten isoforms, is a major component of basement membranes and has been shown to mediate cell-matrix attachment, gene expression, tyrosine phosphorylation of cellular proteins, and branching morphogenesis. See, e.g. Streuli, et al., *J. Cell Biol.*, 129:591–603 (1993); Malinda and Kleinman, *Int. J. Biochem. Cell Biol.* 28:957–1959 (1996); Timpl and Brown, *Matrix Biol.* 14:275–281 (1994); Tryggvason, *Curr. Op. Cell Biol* 5:877–882 (1993); Stahl, et al., *J. Cell Sci.* 110:55–63 (1997). The expression patterns of the laminin isoforms are tissue specific. The laminin-5 isoform (nicein, epiligrin, kalinin) is abundant in transitional epithelium, stratified squamous epithelia, lung mucosa and other epithelial glands. Kallunki, et al., *J. Cell Biol.* 119:679–693 (1992); Jones, et al., unpublished observations. Laminin-5 is a heterotrimer consisting of α3, β3 and γ2 subunits that associate by means of large α-helical regions to produce a cruciform-shaped molecule. Rousselle, et al.,*J. Cell Biol.* 114:567–76 (1991); Baker, et al., J. Cell Sci. 109:2509–2520 (1996).

Laminin-5 is synthesized initially as a 460 kD molecule, which undergoes specific processing to a smaller form after being secreted into the extracellular matrix. Marinkovich, et al., *J. Biol. Chem.,* 267:17900–17906 (1992); Matsui, et al., *J. Biol. Chem.* 270:23496–23503 (1995); Vailly, et al., *Eur. J. Biochem.* 219:209–218 (1994). The size reduction is a result of processing of the α3 and γ2 subunits from 200–190 to 160 kD and from 155 to 105 kD, respectively. Marinkovich, et al., *J. Biol. Chem.,* 267:17900–17906 (1992); Matsui, et al., *J. Biol. Chem.* 270:23496–23503 (1995); Vailly, et al., *Eur. J. Biochem.* 219:209–218 (1994). The proteases involved in these proteolytic events have not been identified.

Laminin-5 has been reported to function in the nucleation of hemidesmosome assembly and as an adhesive factor that retards cell motility. Baker, et al.,*J. Cell Sci.* 109:2509–2520 (1996); O'Toole, et al., *Exp. Cell Res.*, in press. In contrast, some authors have provided evidence that laminin-5 enhances cell motility and is expressed at the migrating edges of certain tumor cell populations. Zhang and Kramer, *Exp. Cell Res.* 227:309–333 (1996); Pyke, et al., *Am. J. Pathol.* 145:782–791 (1994); Pyke, et al., *Cancer Res.* 55:4132–4139 (1995).

In a number of studies, it has been demonstrated that laminin-5 produced by 804G cells can nucleate the assembly of hemidesmosomes by SCC12, HaCaT and pp126 cells, as well as corneal cells maintained in vitro. Langhofer, et al.,*J. Cell Sci.* 105:753–764 (1993); Hormia, et al., *J. Invest. Dermatol.* 105:557–561 (1995); Baker, et al., *J. Cell Sci.* 109:2509–2520 (1996); Baker, et al., *Exp. Cell Res.* 228:262–270 (1996); Tamura, et al.,*J. Periodontal. Res.*, in press. Although SCC12, HaCaT and pp126 cells also secrete laminin-5, the laminin-5 that they secrete is incapable of supporting the assembly of hemidesmosomes.

SUMMARY OF THE INVENTION

The invention is based on the discovery that laminin-5 which promotes hemidesmosome assembly ("hemidesmosome-promoting laminin-5") contains a smaller α3 subunit ("hemidesmosome-promoting α3 subunit") than laminin-5 which does not promote hemidesmosome assembly. The hemidesmosome-promoting α3 subunit is produced by proteolytic cleavage of the unprocessed α3 subunit. The phrase "unprocessed α3 subunit" is used herein to refer to the α3 subunit as it is initially produced by cells and, of course, prior to the proteolytic processing which produces the hemidesmosome-promoting α3 subunit. The invention is also based on the further discovery that laminin-5 comprising the unprocessed α3 subunit promotes epithelial cell migration.

In particular, the invention provides methods of generating hemidesmosome-promoting laminin-5 comprising proteolytic cleavage of the unprocessed α3 subunit of laminin-5 by plasmin. In one embodiment, the method comprises culturing epithelial cells that do not produce hemidesmosome-promoting laminin-5 under conditions effective so that they produce extracellular matrix protein comprising laminin-5 containing unprocessed α3 subunits and contacting the laminin-5 with plasmin under conditions effective so that the plasmin cleaves the α3 subunits. In another embodiment, the method comprises producing heterotrimeric laminin-5 containing unprocessed α3 subunits by expressing DNA coding for α3, γ2 and β3 subunits in host cells transformed with the DNA and contacting the laminin-5 with plasmin under conditions effective so that the plasmin cleaves the α3 subunits. In yet another embodiment, the method comprises contacting a material containing unprocessed α3 subunits of laminin-5, but not γ2 subunits or ϴ3 subunits of laminin-5, with plasmin under conditions effective so that the plasmin cleaves the α3 subunits. The cleaved α3 subunits are combined with γ2 and β3 subunits so that the three subunits combine to form hemidesmosome-promoting laminin-5.

The invention further provides a method of stimulating hemidesmosome assembly by contacting epithelial cells with hemidesmosome-promoting laminin-5 produced by the methods of the invention. It is desirable to grow epithelial cells for various applications on hemidesmosome-promoting laminin-5 since the organization of epithelial cells grown on hemidesmosome-promoting laminin-5 is significantly more advanced and tissue-like than cells grown on laminin-5 which does not promote hemidesmosome formation.

In addition, the invention provides hemidesmosome-promoting laminin-5 and hemidesmosome-promoting α3 subunits of laminin-5. The invention further provides shaped articles coated with hemidesmosome-promoting laminin-5 and pharmaceutical compositions comprising hemidesmosome-promoting laminin-5.

The invention also provides a method of promoting wound healing. The method comprises contacting the wound with an amount of laminin-5 comprising unprocessed α3 subunits which is effective to promote the migration of epithelial cells into the wound. The method may further comprise contacting the wound with an amount of plasmin effective to convert the laminin-5 into hemidesmosome-promoting laminin-5 so that the epithelial cells in the wound are stimulated to assemble hemidesmosomes.

The invention further provides a method of promoting epithelial cell migration. The method comprises contacting epithelial cells with an amount of laminin-5 comprising unprocessed α3 subunits which is effective to promote the migration of the epithelial cells.

In addition, the invention provides a method of promoting epithelialization of a surface. The method comprises contacting the surface with an amount of laminin-5 comprising unprocessed α3 subunits which is effective to promote the migration of epithelial cells over the surface. The method may further comprise contacting the surface with an amount of plasmin effective to convert the laminin-5 into hemidesmosome-promoting laminin-5 so that the epithelial cells on the surface are stimulated to assemble hemidesmosomes.

The invention further provides a pharmaceutical composition. The composition comprises laminin-5 comprising unprocessed α3 subunits and a pharmaceutically-acceptable carrier.

Finally, the invention provides a shaped article having laminin-5 comprising unprocessed α3 subunits applied thereto.

DETAILED DESCRIPTION OF THE PRESENTLY PREFERRED EMBODIMENTS

The invention provides methods of producing hemidesmosome-promoting laminin-5. The hemidesmosome-promoting laminin-5 may be from any animal species. Preferably, however, if the hemidesmosome-promoting laminin-5 is to be administered to an animal, hemidesmosome-promoting laminin-5 from that species of animal is used. Thus, if a human is to be given the hemidesmosome-promoting laminin-5, human laminin-5 is preferably used.

The methods of producing hemidesmosome-promoting laminin-5 comprise contacting a material containing unprocessed α3 subunits of laminin-5 with plasmin under conditions effective so that the plasmin cleaves the α3 subunits to produce hemidesmosome-promoting α3 subunits. Suitable conditions are known or can be determined empirically. In particular, there are a number of potential plasmin cleavage sites in the unprocessed α3 subunits, so conditions should be avoided which give rise to additional cleavages besides the one(s) that produce(s) hemidesmosome-promoting α3 subunits. Notably, prolonged incubation should be avoided, and the reaction should be terminated by adding a plasmin inhibitor and/or by removing the plasmin from the reaction mixture, as is well known in the art. Suitable inhibitors include any serine protease inhibitor (e.g., dichloroisocoumarin). The plasmin may be removed from the reaction mixture by washing or affinity purification.

Plasmin may be produced by contacting plasminogen with a plasminogen activator. The plasminogen may be from any animal species. Preferably, however, if the hemidesmosome-promoting laminin-5 is to be administered to an animal, plasminogen from that species of animal is used. Thus, if a human is to be given the hemidesmosome-promoting laminin-5, human plasminogen is preferably used. Methods of making plasminogen are well known in the art. Plasminogen may also be purchased commercially. Preferably the plasminogen is prepared by recombinant DNA or other techniques that avoid the inclusion of infectious agents in the plasminogen preparation.

All types of plasminogen activators may be used, including urokinase-type plasminogen activators and tissue-type plasminogen activators. Preferably the plasminogen activator is a tissue-type plasminogen activator. The plasminogen activator may be from any animal species. Preferably, however, if the hemidesmosome-promoting laminin-5 is to be administered to an animal, plasminogen activator from that species of animal is used. Methods of making plasminogen activators are well known in the art, and many plasminogen activators are available commercially. Preferably the plasminogen activator is prepared by recombinant DNA or other techniques that avoid the inclusion of infectious agents in the plasminogen activator preparation.

To produce plasmin, the plasminogen is contacted with the plasminogen activator in amounts and under conditions effective to cause the conversion of the plasminogen to plasmin. These amounts and conditions are known or can be determined empirically as is known in the art. The plasmin may be at least partially purified prior to contacting it with the material containing the unprocessed α3 subunit. Methods of purifying plasmin are well known in the art. Plasmin purchased commercially or prepared in other ways may also be used.

The plasmin (whatever its source and whether purified, partially purified or unpurified from the reaction mixture in which it was produced) may be added to the material containing the unprocessed α3 subunits. As noted above, suitable conditions for the plasmin cleavage of the α3 subunits are known or can be determined empirically.

Alternatively, the material containing unprocessed α3 subunits may be contacted with plasminogen and plasminogen activator (added simultaneously or sequentially) under conditions effective so that the plasminogen is converted into plasmin which then cleaves the unprocessed α3 subunits. Suitable conditions are known or can be determined empirically.

Tryptase has been shown to produce cleaved α3 subunits of the same approximate molecular weight as those produced by plasmin cleavage (see Example 2). Although laminin-5 containing tryptase-cleaved α3 subunits has not yet been tested to determine if it promotes hemidesmosome assembly, it seems likely that it will do so, given the similarity in the sizes of the cleaved α3 subunits and the similarities in the two enzymes (plasmin and tryptase). In particular, both plasmin and tryptase are serine proteases that cleave after lysine and arginine residues. Other serine proteases that cleave after lysine and arginine residues are known and include trypsin, thrombin, and others. Thus, in addition to plasmin, other serine proteases cleaving after lysine and arginine residues may be useful in the practice of the invention.

In one embodiment, the material containing the unprocessed α3 subunits is the extracellular matrix protein produced by culturing epithelial cells that do not produce hemidesmosome-promoting laminin-5. Extracellular matrix protein which is deposited (insoluble) or secreted (soluble) may be used. The extracellular matrix protein comprising laminin-5 containing unprocessed α3 subunits may be treated with plasmin, or the laminin-5 may be purified from the extracellular matrix protein and treated with the plasmin. Methods of purifying laminin-5 are known. For instance, an antibody can be used to affinity-purify the laminin-5.

Suitable cells for the production of extracellular matrix include any epithelial cell which does not produce hemidesmosome-promoting laminin-5. For instance, SCC12 squamous cell carcinoma cell line, pp126 transformed oral epithelial cell line, and normal epidermal keratinocytes can be used (see Example 1).

The epithelial cells are cultured and the extracellular matrix produced, as is known in the art. See Spector et al. *Cells: A laboratory manual* (Cold Spring Harbor Press, Cold Spring Harbor, N.Y. 1997). Preferably the cells are removed from the extracellular matrix before the matrix is treated to produce the hemidesmosome-promoting laminin-5. Methods of removing cells from the extracellular matrix are also known in the art. See Gospodarowicz, *Methods for Preparation of Media Supplements and Substrata*, 1:275–293 (D. W. Barnes, et al. eds., A. R. Liss, NY 1984), Carter et al., *Cell*, 65:599–610.

The extracellular matrix may be treated with plasmin as described above. In addition, the extracellular matrix may be contacted with plasminogen and plasminogen activator as described above. In particular, it has been found that plasminogen present in culture medium binds to the laminin-5 in the extracellular matrix (see Example 4). Accordingly, hemidesmosome-promoting laminin-5 can be produced by simply adding plasminogen to the culture medium and, simultaneously or subsequently, adding a plasminogen activator under conditions effective to cause the conversion of plasminogen to plasmin.

Instead of extracellular matrix protein, the material containing the unprocessed α3 subunits may be that material obtained by culturing host cells containing DNA encoding the unprocessed α3 subunits. Materials and methods for producing the unprocessed α3 subunits in this manner are described in detail below. The unprocessed α3 subunits can be recovered from the culture, treated with plasmin as described above, and the cleaved α3 subunits combined with γ2 and β3 subunits to produce the hemidesmosome-promoting laminin-5. Alternatively, the unprocessed α3 subunits may be combined with γ2 and β3 subunits (also produced by recombinant DNA techniques as described below) so that laminin-5 is produced, and the laminin-5 treated with plasmin as described above to produce hemidesmosome-promoting laminin-5. Clones and sequences for the α3, γ2 and β3 subunits are known and available (see below). Also, recombinant DNA methods and suitable host cells, vectors and other reagents for producing laminin-5 subunits in this manner are well known in the art.

The selection of a particular host cell for production of one or more of the laminin-5 subunits is dependent upon a number of factors recognized by the art. These include, for example, compatibility with the chosen expression vector, toxicity of the subunit to the cell, rate of transformation, expression characteristics, bio-safety, and costs. A balance of these factors must be struck with the understanding that not all hosts may be equally effective for the expression of a particular subunit.

Eukaryotic host cells are preferred for making the laminin-5 subunits. Within the above guidelines, useful eukaryotic host cells include yeast and other fungi, animal cell lines, animal cells in an intact animal, insect cells, and other eukaryotic host cells known in the art. Preferred are CHO cells (mammalian) and Drosophila (insect cells).

The host cells may be transformed with a vector comprising DNA encoding one or more laminin-5 subunits. On the vector, the coding sequence(s) must be operatively linked to expression control sequences. As used herein "operatively linked" refers to the linking of DNA sequences in such a manner that the laminin-5 subunit(s) will be expressed. Preferably the linking, including the order of the sequences, the orientation of the sequences, and the relative spacing of the various sequences, is performed so that optimum expression is obtained.

The expression control sequences must include a promoter. The promoter used in the vector may be any sequence which shows transcriptional activity in the host cell and may be derived from genes encoding homologous or heterologous proteins and either extracellular or intracellular proteins. However, the promoter need not be identical to any naturally-occurring promoter. It may be composed of portions of various promoters or may be partially or totally synthetic. Guidance for the design of promoters is provided by studies of promoter structure such as that of Harley and Reynolds, *Nucleic Acids Res.*, 15, 2343–61 (1987). Also, the location of the promoter relative to the transcription start may be optimized. See Roberts, et al., *Proc. Natl Acad. Sci. USA*, 76, 760–4 (1979). The promoter may be inducible or constitutive, and is preferably a strong promoter. By "strong," it is meant that the promoter provides for a high rate of transcription in the host cell.

In the vector, the coding sequences must be operatively linked to transcription termination sequences, as well as to the promoter. The coding sequences may also be operatively linked to expression control sequences other than the promoters and transcription termination sequences. These additional expression control sequences include activators, enhancers, operators, stop signals, cap signals, polyadenylation signals, 5' untranslated sequences, and other sequences and signals involved with the control of transcription or translation.

The consensus sequence for the translation start sequence of eukaryotes has been defined by Kozak (*Cell*, 44, 283–292 (1986)) to be: C(A/G)CCAUGG. Deviations from this sequence, particularly at the −3 position (A or G), have a large effect on translation of a particular mRNA. Virtually all highly expressed mammalian genes use this sequence. Highly expressed yeast mRNAs, on the other hand, differ from this sequence and instead use the sequence (A/Y)A(A/U)AAUGUCU (Cigan and Donahue, *Gene*, 59, 1–18 (1987)). These sequences may be altered empirically to determine the optimal sequence for use in a particular host cell.

DNA coding for a laminin-5 subunit may prepared using standard methods such as those described in Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989). In particular, clones coding for each of the subunits are known and available. See, e.g., Ryan et al., *J. Biol. Chem.* 269:22779–22787 (1984); Kallurki et al., *J. Cell Biol.*, 119:679–693 (1992), Gerecke et al., *J. Biol. Chem.* 269:11073–11080 (1994). Other clones may be identified by methods known in the art. The clones, whether known or newly-identified, may be modified by methods known in the art.

The coding sequences may, alternatively, be synthesized using standard techniques that are well known in the art using the known subunit sequences (see above). For instance, DNA sequences may be synthesized by phosphoamidite chemistry in an automated DNA synthesizer, purified, annealed, ligated and cloned into suitable vectors. Chemical synthesis is preferable for several reasons.

First, chemical synthesis is desirable because codons preferred by the host in which the DNA sequence will be expressed may be used to optimize expression. Not all of the codons need to be altered to obtain improved expression, but greater than 50%, most preferably at least about 80%, of the codons should be changed to host-preferred codons. The codon preferences of many host cells are known. See *Maximizing Gene Expression*, pages 225–85 (Reznikoff & Gold, eds., 1986). The codon preferences of other host cells can be deduced by methods known in the art.

The use of chemically synthesized DNA also allows for the selection of codons with a view to providing unique or nearly unique restriction sites at convenient points in the sequence. The use of these sites provides a convenient means of constructing the synthetic coding sequences. In addition, if secondary structures formed by the messenger RNA transcript or other destabilizing sequences interfere with transcription or translation, they may be eliminated by altering the codon selections.

Chemical synthesis also allows for the use of optimized expression control sequences with the DNA sequence coding for a laminin-5 subunit. In this manner, optimal expression of the subunits can be obtained. For instance, as noted above, promoters can be chemically synthesized and their location relative to the transcription start optimized.

DNA coding for a signal or signal-leader sequence may be located upstream of the DNA sequence encoding the laminin-5 subunits. A signal or signal-leader sequence is an amino acid sequence at the amino terminus of a protein which allows the protein to which it is attached to be secreted from the cell in which it is produced. Suitable signal and signal-leader sequences are well known. Although secreted proteins are often easier to purify, expression levels are generally lower than those that can be obtained in the absence of secretion.

Vectors for expressing the laminin-5 subunits may be any vector which may conveniently be subjected to recombinant DNA procedures and which is capable of expressing a laminin-5 subunit in the selected host cell. The vector used to transform the host cells may have one or more replication systems which allow it to replicate in the host cells. In particular, when the host is a yeast, the vector should contain the yeast 2u replication genes REP 1–3 and origin of replication.

Alternatively, an integrating vector may be used which allows the integration into the host cell's chromosome of the sequence coding for a laminin-5 subunit. Although the copy number of the coding sequence in the host cells would be lower than when self-replicating vectors are used, transformants having sequences integrated into their chromosomes are generally quite stable.

When the vector is a self-replicating vector, it is preferably a high copy number plasmid so that high levels of expression are obtained. As used herein, a "high copy number plasmid" is one which is present at about 100 copies or more per cell. Many suitable high copy number plasmids are known.

The vector desirably also has unique restriction sites for the insertion of DNA sequences and a sequence coding for a selectable or identifiable phenotypic trait which is manifested when the vector is present in the host cell ("a selection marker"). If a vector does not have unique restriction sites, it may be modified to introduce or eliminate restriction sites to make it more suitable for further manipulations.

After the vector comprising a DNA sequence coding for a laminin-5 subunit is prepared, it is used to transform the host cells. Methods of transforming host cells are well known in the art, and any of these methods may be used.

Transformed host cells are selected in known ways and then cultured under conditions effective to produce the laminin-5 subunits. The methods of culture are those well known in the art for the chosen host cell.

The expressed laminin-5 subunits may be recovered using methods of recovering and purifying proteins from recombinant cell cultures that are well known in the art. In particular, antibodies which bind selectively to the laminin-5 subunits may be used to purify the subunits.

Preferably, all three laminin-5 subunits are produced in the same host cell. In this manner, the three subunits will be expressed and assembled into laminin-5. See, Yurcherao et al., *Proc. Nat'l Acad. Sci.* 94:10189–10194 (1997) (production of laminin-1). Alternatively, the subunits can be produced in different host cells, the subunits recovered and contacted under conditions effective to allow the subunits to assemble into laminin-5. The laminin-5 containing unprocessed α3 subunits can be treated with plasmin as described above. Alternatively, the unprocessed α3 subunits can be treated with plasmin, and the cleaved, hemidesmosome-promoting α3 subunits combined with γ2 and β3 subunits so that they assemble into hemidesmosome-promoting laminin-5. Although the γ2 subunits of hemidesmosome-promoting laminin-5 can be processed (see Example 1), this is not necessary for the laminin-5 to promote hemidesmosome assembly (see Example 1). Thus, processed or unprocessed γ2 subunits may used for the production of hemidesmosome-promoting laminin-5.

Human hemidesmosome-promoting α3 subunits have been characterized. They have a molecular weight of about 160 kD (compared to a molecular weight of 190–200 kD for the unprocessed subunit). Also, antibodies prepared against the C-terminus of the unprocessed subunit (residues 1561–1713) did not bind to hemidesmosome-promoting α3 subunits, indicating that plasmin cleaves the unprocessed α3 subunits upstream of the C-terminus (see Example 1). Once additional information about the α3 subunit, preferably the N-terminal and/or C-terminal sequence, is obtained, hemidesmosome-promoting α3 subunit can be produced in host cells transformed with DNA coding for it without the need for plasmin treatment.

Hemidesmosome-promoting laminin-5 can be used to stimulate hemidesmosome assembly by epithelial cells. To do so, the epithelial cells are contacted with the hemidesmosome-promoting laminin-5 whereby the epithelial cells are stimulated to attach to a substrate and produce hemidesmosomes. The epithelial cells may be vertebrate cells, preferably mammalian cells, most preferably human cells. Human skin cells are one example. The contacting step can be performed ex vivo or in vivo. As used herein "stimulating hemidesmosome assembly" includes (1) inducing epithelial cells which do not normally produce hemidesmosomes to produce them; and (2) accelerating the formation of hemidesmosomes by cells that can produce hemidesmosomes.

To stimulate hemidesmosome assembly, a substrate upon which cells are to be grown is coated with the hemidesmosome-promoting laminin-5. The epithelial cells are then applied to the substrate and grown on the hemidesmosome-promoting laminin-5. Such cells, including human cells in vitro and in vivo, will grow in an organized fashion on the substrate and will form hemidesmosomes. Hemidesmosome formation is a major advantage because it greatly enhances the attachment of the cells to the substrate.

The substrates useful in the invention may be any desired substrate. For laboratory use, the substrate may be as simple as glass or plastic. For use in vivo, the substrate may be any biologically compatible material on which cells can grow. Suitable substrate materials include shaped articles made of, or coated with, materials such as collagen, polylactic acid, polyglycolic acid, other bioerodible materials, biocompatible metals (such as stainless steel and titanium), ceramic materials (including prosthetic materials such as hydroxylapatite), synthetic polymers (including polyesters and nylons), and virtually any other material to which biological molecules can readily adhere. The shaped articles include such forms as sheets, fabrics, prostheses, metal articles, bioerodible articles, and transplantable or implantable articles. For instance, the shaped article may be an indwelling catheter, colostomy tube, surgical mesh, implantable prosthesis (e.g., a dental prosthesis or a joint prosthesis), needle, screw, plate, metal pin, metal rod, ocular lens, enhancement implant, or other medical device.

A specific use of the present invention is for generating skin for allograft use. Epidermal cells, for example, are seeded onto a substrate of the present invention. These cells are grown on the substrate using conventional skin growth conditions, including nutrients and growth factors. The improvement of the present invention, the use of the hemidesmosome-promoting laminin-5 on the substrate, improves such ex vivo growth of skin over previously described techniques that do not use this laminin-5.

One particular use of the present invention is the augmentation of epidermal cell adhesion to target surfaces. For example, dental implants may be coated with the hemidesmosome-promoting laminin-5 to stimulate periodontal cell attachment. Existing teeth may also be coated with the laminin-5 as a treatment for gum (junctional epithelium) disease, such as gingivitis. Where a substrate is made of a natural or synthetic bioerodible material in the form of a sheet or fabric, such as woven or bonded collagen or polylactic acid, the hemidesmosome-promoting laminin-5 may be applied to the surface thereof or admixed with the composition. Cells may then be grown on the substrate ex vivo to form transplantable or implantable materials. Alternatively, the materials may be implanted and cells may be permitted to attach in vivo.

In addition, the present invention also includes coating shaped articles with hemidesmosome-promoting laminin-5 produced by the above-described techniques. Preferably, the shaped articles are formed of materials other than glass, and include such forms as sheets, fabrics, prostheses, metal articles, bioerodible articles, and implantable articles (see above).

The invention further provides a method of promoting wound healing. In this process, it is necessary for epithelial cells to both cover the wound (i.e., migrate over the wound bed) and then establish adherence, via hemidesmosomes, with the wound bed. Without hemidesmosomes, the cells may come off by simple abrasion.

The method of promoting wound healing comprises contacting the wound with an amount of laminin-5 comprising unprocessed α3 subunits which is effective to promote the migration of epithelial cells into the wound. The laminin-5 can be produced as described above. The method may further comprise contacting the wound with an amount of plasmin effective to convert the laminin-5 into hemidesmosome-promoting laminin-5 so that the epithelial cells in the wound are stimulated to assembly hemidesmosomes. Suitable amounts of laminin-5 and plasmin and suitable conditions may be determined empirically, as is known in the art.

The method of promoting wound healing is based on the discovery that laminin-5 comprising unprocessed α3 subunits promotes the migration of epithelial cells and epithelialization of the wound bed. Thus, laminin-5 comprising unprocessed α3 subunits can be used in other situations to promote the migration of epithelial cells and the epithelialization of other surfaces. These other surfaces could include the surfaces of shaped articles (see above) and surfaces in vivo other than wounds (e.g., the surfaces of teeth as a treatment for gum disease). As in the case of wound healing the surface could subsequently be treated with plasmin to convert the laminin-5 into hemidesmosome-promoting laminin-5 so that the epithelial cells that have migrated onto the surface would be stimulated to assemble hemidesmosomes and adhere better to the surface.

Pharmaceutical preparations of laminin-5 comprising unprocessed α3 subunits and of hemidesmosome-promoting laminin-5 are contemplated. These preparations can be in any suitable form, and comprise the laminin-5 in combination with any of the well known pharmaceutically-acceptable carriers. Carriers include injectable carriers, topical carriers, transdermal carriers and the like. The preparation may advantageously be in a form for topical administration, such as an ointment, gel, cream, spray, dispersion, suspension or paste. The preparations may further include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton, Pa. (1975).

EXAMPLES

Example 1
The Nature of Hemidesmosome-Promoting Laminin-5

The rat epithelial cell line 804G and the human breast epithelial cell line MCF-10A both assemble cell-matrix attachment devices called hemidesmosomes when maintained in tissue culture. Stahl, et al., *J. Cell Sci.* 110:55–63 (1997); Riddelle, et al., *J. Cell Biol.* 112:159–68 (1991). Recent data indicate that this property is dependent upon the laminin-5 secreted by these cells. Baker, et al., *J. Cell Sci.* 109:2509–2520 (1996); Stahl, et al., *J. Cell Sci.* 110:55–63 (1997); Tamura, et al., *J. Periodontal. Res.*, in press. However, laminin-5 is expressed by many other cell types, such as the squamous cell carcinoma line SCC12 and the transformed oral epithelial cell line called pp126, which do not assemble hemidesmosomes under normal conditions. Langhofer, et al., *J. Cell Sci.* 105:753–764 (1993); Baker, et al., *J. Cell Sci.* 109:2509–2520 (1996); Tamura, et al., *J. Periodontal. Res.*, in press. In addition to expressing laminin-5, both SCC12 and pp126 cells express all the major known protein components of hemidesmosomes, yet only assemble hemidesmosomes when plated onto laminin-5 secreted by 804G cells or MCF-10A cells. Langhofer, et al., *J. Cell Sci.* 105:753–764 (1993); Baker, et al., *J. Cell Sci.* 109:2509–2520 (1996); Tamura, et al., *J. Periodontal. Res.*, in press; Jones, unpublished observations. In view of the foregoing, the subunit composition of laminin-5 secreted by 804G, MCF-10A, pp126, SCC12 cells, as well as a "normal" cell population (NHEK), was analyzed by Western immunoblotting using a panel of antibodies against specific laminin-5 subunits.

A. Cell Culture and Preparation of Laminin-5 Matrices

MCF-10A cells (available from the American Type Culture Collection (ATCC), Rockville, Md.; accession number ATCC CRL 10317) and 804G cells (available from ATCC, accession number ATCC CRL 11555) were maintained as described previously. Stahl, et al., *J. Cell Sci.* 110:55–63 (1997); Riddelle, et al., *J. Cell Biol.* 112:159–68 (1991). Normal human epidermal keratinocytes (NHEK, purchased from Clonetics Corp., San Diego, Calif.), SCC12 cells and pp126 cells (both a gift from Dr. Dolphine Oda of the University of Washington) were maintained in the serum-free growth medium Keratinocyte-SFM (Gibco BRL, Gaithersburg, Md.) supplemented with 20 mM L-glutamine, 100 U/ml penicillin, 100 µg/ml streptomycin, 5 ng/ml epidermal growth factor (EGF, Collaborative Research Products, Becton Dickinson Labware, Bedford, Mass.), and 50 µg/ml bovine pituitary extract (Collaborative Research Products, Bedford, Mass.). MCF10A, pp126, SCC12, NHEK and 804G extracellular matrices were prepared as described previously. Gospodarowicz, in *Methods for Preparation of Media Supplements and Substrata*, vol. 1 (Barnes, et al. eds., 1984), pp. 275–293,; Langhofer, et al., *J. Cell Sci.* 105:753–764 (1993). Laminin-5 comprises at least 80% of the protein in such matrix preparations.

B. SDS-PAGE and Western Immunoblotting

Protein preparations (approximately 10 µg of matrix protein per lane) were separated by the method of Laemmli, *Nature(Lond)* 277:680–685 (1970) in 6% acrylamide gels and then transferred to nitrocellulose as described in Harlow and Lane, *Antibodies: A Laboratory Manual*, pp. 92–121, (1988). The nitrocellulose membranes were processed for blotting as described in Zackroff, et al., *J. Cell Biol.* 98:1231–1237 (1984). Blots were developed either using chloronaphthol as a colorimetric reagent or using the Lumi-Glo chemiluminescence kit (Kirkegaard and Perry Laboratories, Gaithersburg, Md.).

C. Antibodies

The mouse monoclonal antibody against the γ2 chain of human laminin-5, GB3, was purchased from Harlan Bioproducts for Science, Inc., Indianapolis, Ind. (Verrando, et al., *Exp. Cell Res.* 170:116–128 (1987); Matsui, et al., *J. Invest. Dermatol.* 105:648–652 (1995)).

For production of a rabbit serum against the human γ2 chain, a clone encoding amino acids 522 through 722 of human laminin-5 γ2 chain was identified in a λgt11 keratinocyte expression library (Clontech Labs, Inc., Palo Alto, Calif.) as detailed in Langhofer, et al., *J. Cell Sci.* 105:753–764 (1993). A 25 ml culture of Y1090 (Stratagene, La Jolla, Calif.) was grown at 37° C. in shaking suspension to an OD of 0.7 and was subsequently inoculated with $10^8$ phage containing the laminin-5 γ2 insert. After one hour, isopropyl-β-D-thiogalactopyranoside (IPTG) was added to a concentration of 1 mM and incubation continued for an additional three hours. Cells were pelleted and resuspended in gel sample buffer (8 M urea, 1% SDS in 10 mM Tris-HCl, pH 6.8, 5% β-mercaptoethanol). The resulting protein sample was then processed for SDS-PAGE, simultaneously with a protein sample derived from non-IPTG-induced cells. Following staining of the gel, a prominent protein migrating at about 14 kD (i.e. a portion of laminin-5 γ2 chain fused with β-galactosidase) was observed exclusively in the induced cells. This polypeptide was excised, rinsed in PBS and then used to immunize a rabbit for polyclonal antibody production. Harlow and Lane, in *Antibodies: A Laboratory Manual*, pp. 92–121 (1988). Blood was collected from the rabbit at three-week intervals. This antiserum was designated J20.

Clone 17, a mouse monoclonal antibody specific for the β3 chain of human laminin-5, was purchased from Transduction Laboratories (Lexington, Ky.).

The mouse monoclonal antibody 10B5, which recognizes the α3 subunit of rat and human laminin-5, was generated using 804G laminin-5 as immunogen as described in Langhofer, et al., *J. Cell Sci.* 105:753–764 (1993); Baker et al., *J. Cell Sci.* 109:2509–2520 (1996).

J21 antiserum was prepared against MCF-10A matrix (Langhofer et al., *J. Cell Sci.* 105:753–764 (1993)) and shows reactivity with all three laminin-5 subunits, but does not recognize other laminin isoforms or fibronectin.

For production of serum antibodies against the COOH-terminal region of the human laminin-5 α3 subunit, a 535-base pair HindIII/XhoI cDNA fragment encoding amino acid residues 1561–1713 of the G5 domain of the α3 subunit was subcloned into the HindIII and XhoI sites of the pET32b vector (Novagen, Inc., Madison, Wis.) adjacent a His-tag region and then transfected into DE3αcells (Ryan et al., *J. Biol. Chem.*, 269, 22779–22787 (1994)). Selection was with ampicillin antibiotic (Fisher Scientific, Pittsburgh, Pa.). A histidine (His) fusion protein was induced with 1 mM IPTG (Sigma Chemical Co., St. Louis, Mo.), and then the cells expressing the fusion protein were extracted in SDS buffer (8M urea, 1% SDS in 10 mM Tris-HCl, pH 6.8, 5% β-mercaptoethanol). The fusion protein was identified by Western blotting using a His-HRP probe (SuperSignal His-Probe Western blotting kit; Pierce Chemical Co., Rockford, Ill.) and on an SDS-PAGE gel after protein staining in Coomassie brilliant blue (Sigma Chemical Co., St. Louis, Mo.). The protein was excised from the gel and then the gel pieces were homogenized and subsequently injected into BALB/c mice for generation of mouse antisera. One such serum (Cta3) was used in the course of these studies, although all of the sera showed the same immunoblotting reactivities.

D. Results

Clone 17 monoclonal antibody against the β3 subunit of laminin-5 recognized a band migrating at 145 kD present in MCF-10A, SCC12, NHEK and pp126 cell matrices. This monoclonal antibody, which does not recognize the β3 subunit of rat laminin-5, did not react with the 804G cell matrix preparation.

The rabbit polyclonal antibody J20, recognizing the γ2 subunit of human laminin-5 and displaying cross-reactivity with the rat homologue, detected 155 kD and 105 kD polypeptides in the matrices produced by MCF-10A, 804G, pp126 and NHEK cells, but only a 105 kD species in the matrix produced by SCC12 cells.

For the analysis of the α3 chain of laminin-5, mouse monoclonal antibody 10B5 was used. 10B5 specifically recognized the α3 chain of rat laminin-5 and displayed cross-reactivity with the α3 subunit of the human homologue. The α3 subunits of pp126, SCC12 and NHEK laminin-5 migrated at 190 kD, identical to the reported size of the unprocessed α3 chain of laminin-5. Marinkovich, et al., *J. Biol. Chem.*, 267:17900–17906 (1992); Matsui, et al., *J. Biol. Chem.* 270:23496–23503 (1995). The appearance of the unprocessed α3 subunit of laminin-5 in NHEK matrix had not previously been noted. Marinkovich, et al., *J. Biol. Chem.*, 267:17900–17906 (1992); Matsui, et al., *J. Biol. Chem.* 270:23496–23503 (1995). In contrast, in the matrices of MCF-10A and 804G cells, the α3 chain migrated at 160 kD, similar to the molecular weight of the processed α3 chain subunit. Marinkovich, et al., *J. Biol. Chem.*, 267:17900–17906 (1992); Matsui, et al., *J. Biol. Chem.* 270:23496–23503 (1995).

These results indicate that there is no obvious correlation between the sizes of the γ2 or β3 subunits of laminin-5 and the ability of a cell to assemble a hemidesmosome. In contrast, the matrices of those cells (MCF-10A and 804G) that assemble hemidesmosomes contained processed (160 kD) α3 subunits, while matrices of those cells (pp126, SCC12 and NHEK) that do not assemble hemidesmosomes contain unprocessed (190 kD) α3 subunits.

To test the possibility that plasmin cleavage occurs towards the COOH terminus of the α3 subunit of laminin-5, antiserum Cta3 against residues 1561–1713 at the COOH terminus of the α3 subunit was used. Cta3 antiserum showed reactivity with the 190-kD unprocessed form of the α3 subunit present in pp126 matrix, but failed to show reactivity with any species in MCF-10A matrix. In contrast, the 10B5 monoclonal antibody recognized the unprocessed 190-kD α3 subunit in pp126 matrix as well as the processed 160-kD species in MDF-10A matrix in a comparable immunoblot. Although these results do not rule out the possibility there may be a plasmin cleavage site close to the $NH_2$ terminus of the molecule, it provides direct evidence that plasmin cleaves the 190-kD α3 subunit towards its COOH terminus to produce the hemidesmosome-promoting 160-kD α3 subunit.

Example 2
Plasmin Cleavage Produces Hemidesmosome-Promoting Laminin-5

Certain proteinases were tested for their ability to alter the electrophoretic mobility of the laminin-5 α3 subunit of pp126, SCC12 and NHEK matrices, as determined by Western immunoblotting. Plasmin, matrix metalloproteinase-2 (MMP-2, gelatinase A) and matrix metalloproteinase-9 (MMP-9, gelatinase B), which have been observed by the inventors to be expressed by these cells, were tested. Also, mast cell tryptase which, like plasmin, is a trypsin-like serine proteinase, was tested.

Plasmin was purified as previously described (Stack, et al., *Cancer Res.* 53:1998–2004 (1993); Stack and Pizzo, *Arch. Bioch. Biophys.* 309:117–122 (1994); Stack, et al., *Eur. J. Biochem.* 226:937–943 (1994)). MMP-2 and MMP-9 were obtained from the serum-free conditioned medium of epithelial ovarian carcinoma cells as previously described (Young et al., *Gyn. Onc.* 62:89–99 (1996)) or were the generous gift of Dr. Hideaki Nagase of the University of Kansas. Mast cell tryptase was provided by Dr. David Johnson of East Tennessee State University (Little and Johnson, *Biochem. J.* 307:341–346 (1995)).

The matrices were prepared as described in Example 1. Cells were removed from their matrix with 20 mM ammonium hydroxide, as previously described. Gospodarowicz, in *Methods For Preparation of Media, Supplements And Substrata*, volume 1, pages 275–293 ( Barnes et al. eds. 1984). Then, the matrix was extensively washed with phosphate buffered saline (PBS), and approximately 50 μg of matrix were incubated with: (i) 1 ml of PBS containing plasmin at concentrations of 0.01, 0.1 and 1 μg/ml for 90 min at 37° C.; (ii) 1 ml of PBS containing 5 μg/ml of either MMP-2 or MMP-9 overnight at 37° C.; or (iii) 1 ml of PBS containing 1 μg/ml of tryptase for 90 minutes at 37° C. The serine proteinase inhibitor, dichloroisocoumarin (DCI; Sigma Chemical Co., St. Louis, Mo.), was then added to the treated matrix at 10 μg/ml, for 15 minutes at room temperature. After washing with PBS, the treated matrices were solubilized in sample buffer consisting of 8 M urea, 1% sodium dodecyl sulfate in 10 mM Tris-HCl, pH 6.8, and 15% β-mercaptoethanol. The solubilized matrices were subjected to Western immunoblotting, performed as described in Example 1.

MMP-2 and MMP-9 at enzyme-substrate ratios of about 1:10 exhibited no obvious effect on any of the laminin-5 subunits of pp126 matrix. Also, plasmin at concentrations of 0.01 and 0.1 μg/ml had no obvious effect on the laminin-5 subunits of pp126 matrix. However, following treatment of pp126 matrix with plasmin at 1 μg/ml, the α3 subunit was converted from a 190 kD species to a 160 kD species. This treatment did not induce proteolysis of the γ2 or β3 subunits of laminin-5 (molecular weights of 100 and 145 kD, respectively, with or without plasmin treatment). Also, treatment of pp126 matrix with tryptase at 1 μg/ml converted the α3 subunit from a 190 kD species to a 160 kD species. The results obtained using the other cell lines were identical to those obtained with pp126 cells.

Example 3
Functional Consequences of Processing of the α3 Subunit of Laminin-5

This example describes the effect of plasmin treatment of laminin-5 on the ability of laminin-5 to affect cell motility and hemidesmosome assembly.

A. Cell Motility Assay

The motility of SCC12 cells plated on the laminin-5-rich matrix of pp126 cells was assessed relative to their motility on MCF-10A matrix. The cell matrices were prepared as described in Example 1, and the pp126 and MCF-10A cells removed from their matrices as described in Example 2. The pp126 matrix was treated with plasmin at a concentration of 1 μg/ml as described in Example 2, except that the matrix was not solubilized after plasmin treatment.

SCC12 cells in medium containing 20 mM (N-[2-hydroxyethylpiperazine-N'-[2-ethanesulfonic acid]) (HEPES) were plated onto matrix for 1 hour. They were subsequently maintained at 37° C. and viewed by phase contrast microscopy using a Nikon Diaphot system. The field was photographed every five minutes over a two hour period with a chilled CCD camera (Hamamatsu Photonic Systems Corp., Park Ridge, Ill.). The location of each cell was translated into numerical coordinates using the public domain NIH Image Program, and motility for each cell was calculated as displacement in micrometers from the starting point to the ending point. An average of 30 cells was monitored for each trial.

SCC12 cells plated onto MCF-10A matrix exhibited lower motility after two hours compared with SCC12 cells plated onto pp126 matrix. SCC12 cells plated onto plasmin-modified pp126 matrix displayed motility 2.5 to 3 fold lower than motility on untreated matrix and similar to the motility observed on MCF-10A matrix. The differences in motility of SCC12 cells on these distinct matrices were statistically significant as determined using the non-parametric ANOVA Mann-Whitney U test.

Cell motility on laminin-5 affinity-purified from pp126 matrix was also assessed. For affinity purification of pp126 laminin-5, tissue culture plastic was coated with 50 μg/ml GB3 antibody (see Example 1) in 10 mM Tris, pH 7.4, overnight at 4° C. Dishes were rinsed briefly with phosphate buffered saline, then incubated with conditioned medium (CM) from pp126 cells for one hour at 37° C. To prepare the pp126 CM, pp126 cells were allowed to grow to confluence in medium, the medium was removed, cell debris was collected by centrifugation, and the supernatant (CM) was collected. The dishes were then washed in 20 mM Tris, pH 7.4, containing 250 mM NaCl, followed by three washes in 10 mM Tris, pH 7.4. Affinity-purified laminin-5 was treated with plasmin at a concentration of 1 μg/ml as described in Example 2, except that the affinity-purified laminin-5 was not solubilized.

SCC12 cells plated onto plasmin-treated, affinity-purified laminin-5 also showed 2.4 fold lower motility than SCC12 cells plated onto affinity-purified, untreated pp126 laminin-5. The difference in motility of SCC12 cells on affinity-purified laminin-5 compared with that on plasmin-treated, affinity-purified laminin-5 showed statistical significance at p<0.008 as determined using the non-parametric ANOVA Mann-Whitney U test.

To assess the purity of the affinity-purified laminin-5, confluent dishes of pp126 cells were radiolabeled overnight with 50 mCi/ml of $^{35}$S-PRO-MIX cell label (Amersham Corp., Arlington Heights, Ill.). The labeled conditioned medium was then overlaid on the GB3 antibody-coated dishes and processed as described above. After washing, the proteins "captured" by the antibody were solubilized in SDS-PAGE sample buffer and resolved by SDS-PAGE. The gels were dried and exposed to X-Omat Imaging Film (Eastman Kodak).

By SDS-PAGE, the affinity-purified untreated pp126 laminin-5 consisted of three distinct polypeptides of 190, 145 and 100 kD, representing the α3, β3, and γ2 subunits, respectively. In the plasmin-modified material, the α3 subunits migrated around 160 kD, whereas the β3 and γ2 subunits showed no change in their electrophoretic mobility. These results were confirmed by Western immunoblotting.

Since there is evidence that laminin-5 is complexed with two recently identified laminin isoforms, laminin-6 and laminin-7, the presence of these other laminin variants in pp126 matrix was determined by Western immunoblotting using monoclonal antibody 1921 (purchased from Chemicon International, Inc., Temecula, Calif.) specific for β1 subunit of laminin-6 and laminin-7. It was found that pp126 matrix contained little or no laminin-6 or laminin-7.

B. Hemidesmosome Formation

Laminin-5 is the extracellular ligand of the integrin pairs α6β4 and α3β1. Carter, et al., *Cell* 65:599–610 (1991); Niessen, et al., *Exp. Cell Res.* 211:360–367 (1994). The precise physiological role of α3β1 integrin-laminin-5 ligation is unknown, whereas the α6β4 integrin-laminin-5 complex forms the core of hemidesmosomes. Stepp, et al., *Proc. Natl. Acad. Sci.* 87:8970–8974 (1990); Jones, et al., *Exp. Cell Res.* 213:1–11 (1994); Green and Jones, *FASEB J.* 10:871–880 (1996); Borradori and Sonnenberg, *Curr. Op. Cell Biol.* 8:647–656 (1996). It was, therefore, investigated whether SCC12 cells would be induced to assemble hemidesmosomes on either untreated pp126 laminin-5-rich matrix, plasmin-modified pp126 laminin-5-rich matrix, untreated affinity-purified pp126 laminin-5, or plasmin-modified, affinity-purified pp126 laminin-5.

The matrices were prepared and treated, and the SCC12 cells were plated onto these matrices, as described above. After 24 hours, the cells were fixed in 1% glutaraldehyde in 0.1 M sodium cacodylate buffer, pH 7.2, for a minimum of 30 minutes. Fixed preparations were washed three times in 0.1 M sodium cacodylate buffer, pH 7.2, and post-fixed in 1% osmium tetroxide containing 0.8% potassium ferricyanide. Samples were then stained with uranyl acetate, dehydrated six times in ethanol, and embedded in Epon-Araldite resin (Tousimis Corp., Rockville, Md.). Sections were cut perpendicular to the substratum and viewed on a JEOL 1220 electron microscope at 60 kV to assess hemidesmosome assembly (Riddelle, et al., *J. Cell Biol.* 112:159–68 (1991)). Morphometric analyses were performed using the software of the microscope. For each matrix, at least 15 cells in at least two different trials were evaluated for hemidesmosome assembly.

The results for one complete trial are presented in Table 1. SCC12 cells maintained on untreated pp126 matrix or untreated, affinity-purified pp126 laminin-5 assembled few hemidesmosomes at their basal surface and those that occurred appeared "immature." An "immature" hemidesmosome is defined herein as an electron-dense structure, located along the cell-substrate interface, that has a poorly-developed cytoplasmic plaque lacking a tri-layered appearance and obvious keratin bundle association (Langhofer et al., *J. Cell Sci.* 105:753–764 (1993)). In contrast, SCC12 cells plated onto plasmin-modified pp126 matrix or plasmin-modified, affinity-purified pp126 laminin-5 readily assembled "mature" hemidesmosomes. These hemidesmosomes possessed triangular-shaped, tri-layered, electron-dense cytoplasmic plaques and were associated with the keratin intermediate filament cytoskeleton. These data support the conclusion that plasmin processing of laminin-5 activates the ability of laminin-5 to nucleate assembly of hemidesmosomes.

To provide further confirmation that laminin-5 was involved in nucleation of mature hemidesmosome assembly in this system, the hemidesmosome assembly in SCC12 cells maintained for 24 hours on plasmin-modified pp126 matrix or plasmin-modified, affinity-purified laminin-5, both of which had been incubated for 30 minutes at 37° C. with 50 μg/ml of the laminin-5 blocking monoclonal antibody (mAb)1947 (Chemicon Int., Inc., Tenecula, Calif.), was assessed. Antibody treatment of the laminin-5 preparations considerably reduced the formation of mature hemidesmosomes in SCC12 cells (see Table 1).

TABLE 1

Hemidesmosome Assembly in SCC12 cells maintained for 24 hours on various matrices

| Matrix | # of cells evaluated | Immature HDs | Immature HDs/ 100 microns | Mature HDs | Mature HDs/ 100 microns |
| --- | --- | --- | --- | --- | --- |
| pp126 cell ECM | 19 | 34 | 12.72 | 3 | 1.12 |
| pp126 cell ECM + plasmin | 18 | 23 | 7.66 | 128 | 42.64 |
| pp126 cell ECM + plasmin + 1947 mAb | 19 | 33 | 13.5 | 24 | 9.82 |
| Affinity-purified laminin-5 | 19 | 37 | 9.94 | 0 | 0 |
| Affinity-purified laminin-5 + plasmin | 20 | 23 | 6.24 | 53 | 14.38 |
| Affinity-purified laminin-5 + 1947 mAb | 15 | 26 | 8.37 | 7 | 2.25 |

The results in parts A and B of this example demonstrate that laminin-5 which contains an unprocessed α3 subunit supports cell motility and does not induce hemidesmosome assembly. Upon plasmin-mediated proteolytic cleavage of the α3 subunit, the laminin-5 molecule becomes competent to trigger the assembly of hemidesmosomes, leading to decreased cell motility.

Example 4

Plasminogen and tPA Interaction with Laminin-5

Plasmin is generated by cleavage of the proenzyme plasminogen. The cleavage of plasminogen to produce the functional enzyme plasmin is mediated by either of two plasminogen activators designated tissue-type (tPA) and urinary-type (uPA) plasminogen activators. Since colocalization of enzyme and substrate is an important regulatory property governing matrix remodeling, it was determined whether plasminogen and either tPA or uPA are associated in vivo with laminin-5.

MCF-10A and pp126 cells were processed for indirect double-label immunofluorescence microscopy using antibodies against laminin-5 (described in Example 1) in combination with either an antibody against plasminogen, tPA or uPA. Anti-human plasminogen rabbit antiserum was prepared as described in Stack, et al., *Cancer Res.* 53:1998–2004 (1993); Stack and Pizzo, *Arch. Bioch. Biophys.* 309:117–122 (1994); Stack, et al., *Eur. J. Biochem.* 226:937–943 (1994). Monoclonal antibody PAM-3 against human tPA and monoclonal antibody 394 against human uPA were purchased from American Diagnostica Inc. (Greenwich, Conn.).

For the immunofluorescence, MCF-10A and pp126 cells were maintained on glass coverslips for 24–48 hours, then permeabilized in acetone at −20° C. for two minutes and air dried. Coverslips were incubated with a mix of primary antibodies diluted in PBS at 37° C. in a humid chamber for one hour, washed three times in PBS, and incubated for an additional hour at 37° C. with the appropriate mix of secondary antibodies conjugated to rhodamine and FITC. Mounted glass coverslips were viewed using a Zeiss LSM10 laser scanning confocal microscope (Zeiss Inc., Thornwood, N.Y.). Images were stored on Sony optical discs and printed on a Tektronix printer (Tektronix, Wilsonville, Oreg.).

Laminin-5 antibodies generated staining patterns in "circles and arcs" at the basal aspect of the cells. In addition, some staining was also seen in areas of the glass coverslip not covered by cells, as reported previously. Rousselle, et al., *J. Cell Biol.* 114:567–76 (1991); Baker, et al., *J. Cell Sci.* 109:2509–2520 (1996n); Stahl, et al., *J. Cell Sci.* 110:55–63 (1997).

Interestingly, plasminogen staining in both MCF-10A and pp126 cell cultures colocalized almost exactly with laminin-5. The plasminogen is believed to be derived from the bovine pituitary extract used in the culture medium; it is not believed to be synthesized by the cells.

In MCF-10A cells, the monoclonal antibody against tPA, PAM-3, showed an almost identical staining pattern to that generated by antiserum against laminin-5. MCF-10A cells and underlying matrix did not stain positively for uPA or its cell surface receptor, uPAR, suggesting that uPA is not involved in plasmin-mediated laminin-5 processing in vivo, at least in this cell type. Antibodies to uPAR were obtained from American Diagnostica, Inc. (Greenwich, Conn.)

In pp126 cells, tPA did not localize to the matrix of pp126 cells, although it showed weak staining of cell bodies. The cell bodies of pp126 cells, but not matrix, were also stained by the uPA antibody, while the cells show no staining with the antibody against uPAR.

These results suggested the possibility that lack of tPA in the matrix of pp126 cells precludes conversion of plasminogen to plasmin and the subsequent plasmin-mediated α3 chain processing in pp126 cell matrix. It was, therefore, investigated whether addition of purified tPA to pp126 matrix could induce cleavage of the pp126 laminin-5 α3 subunit.

MCF-10A and pp126 matrices were prepared as described in Example 1. For the tPA treatment, 50 μg of the pp126 matrix were treated overnight (16 hours) at 37° C. with 1 ml of PBS containing either 5 or 10 μg/ml tPA. Purified two-chain tPA was the generous gift of Dr. Henry Berger, Wellcome Research Laboratories, Research Triangle Park, N.C. After the tPA treatment, the matrix was treated with DCI, washed and solubilized as described in Example 2. Then, Western immunoblotting was performed (as described in Example 1) on MCF-10A matrix, pp126 matrix (untreated), and the tPA-treated pp126 matrix using antibody 10B5 specific for laminin-5 α3 subunit. Also, cell motility measurements were made as described in Example 3.

Western immunoblotting revealed that tPA treatment of pp126 matrix caused the production of a 160 kD laminin-5 α3 subunit which comigrated with the laminin-5 α3 subunit in MCF-10A matrix. Untreated pp126 matrix contained an unprocessed 190 kD laminin-5 α3 subunit. In addition, SCC12 cells showed lower migration on the tPA-treated pp126 matrix than on untreated matrix. These results were statistically significant.

The observed colocalization of tPA and plasminogen with laminin-5 in fixed MCF-10A cell matrix also suggested that both might bind directly to laminin-5. This was confirmed using a dot blot overlay assay.

For overlay assays, 1 ng of human laminin-5 purified from MCF-10A matrix (provided by Desmos Inc., San Diego, Calif.) and the control proteins fibronectin and BSA were dotted onto nitrocellulose, which was then blocked with PBS containing 0.2% fish gelatin. The membrane was subsequently incubated overnight with 20 μg/ml of either tPA, uPA or plasminogen, at 4° C. with vigorous shaking. The nitrocellulose was then blocked in 5% milk in PBS and processed for immunoblotting, performed as described in Example 1, using antibodies to tPA, plasminogen or uPA (see above). Plasminogen was purified as previously described. Stack, et al., *Cancer Res.* 53:1998–2004 (1993); Stack and Pizzo, *Arch. Bioch. Biophys.* 309:117–122 (1994); Stack, et al., *Eur. J. Biochem.* 226:937–943 (1994). The uPA was purchased from Calbiochem (La Jolla, Calif.).

It was found that tPA bound to laminin-5 and to fibronectin. Plasminogen bound only to laminin-5. Further, uPA bound BSA and fibronectin and bound poorly to laminin-5.

Example 5

Wound Healing

This example provides data demonstrating the involvement of the two forms of laminin-5 (one form comprising an unprocessed α3 subunit and the other form comprising a processed hemidesmosome-promoting α3 subunit) in wound healing. This example also provides data showing the involvement of two integrins in wound healing, and a model of wound healing based on the interaction of the two forms of laminin-5 with these two integrins is presented.

A. In vitro Scrape Wound Assays

MCF-10A cells were grown to confluence either on tissue culture-treated plastic, or on glass coverslips. Medium was aspirated, and the cell-coated surface was scraped with a pipet tip in either a single stripe or a grid pattern. The scrape-wounded surface was washed with PBS and incubated in trypsin at 37° C. for 30 seconds to remove debris from the wound area and wound edges. The surface was washed again twice with serum-containing medium, and then the wounds in the cultures were allowed to heal for various times. For antibody-blocking studies of wound healing, confluent cell cultures were scrape-wounded as above, then culture medium containing the appropriate antibodies was added to the culture. In some experiments, antibody-blocked scrape-wounded cultures were fixed after a set time and processed for immunofluorescence as described below.

B. Skin Wound Specimens

Patients participating in this study were undergoing laser resurfacing for the treatment of wrinkles and discolorations. Briefly, patients were pretreated with Retin-A micro or Renova (Ortho Pharmaceutical Corp., Raritan, N.J.) followed by treatment of the preauricular sites two weeks later with a Nidek Unipulse $CO_2$ laser (Fremont, Calif.). The eschar was removed manually with a saline-soaked gauze between passes, and the laser-treated face was occluded with Flexzan (Dow Hickam Pharmaceuticals Inc., Sugarland, Tex.). Preauricular punch biopsies (3 mm) were taken two days post-resurfacing. The specimens were frozen in Tissue-Tek O.C.T. Compound (Miles, Elkhart, Ind.) and were stored at $-70°$ C. Consecutive frozen sections of 6 $\mu$m thickness were prepared using a Reichert-Jung Leica cryostat at $-20°$ C. and placed on slides. Sections were either extracted in methanol at $4°$ C. for 10 minutes, or fixed in 3.7% formalin at $25°$ C. for 8 minutes followed by a 5 minute extraction in 0.1% SDS. Sections were then processed for indirect immunofluorescence as described below, mounted with Vectashield mounting medium (Vector Laboratories, Burlingame, Calif.), and sealed.

C. Antibodies

For a description of monoclonal antibodies GB3 and 10B5, see Example 1.

J18 polyclonal antisera was raised in a rabbit using rat laminin-5 purified from extracellular matrix preparations of 804G cells, as previously described (Langhofer et al., *J. Cell Sci.*, 105:753–764 (1993)).

A monoclonal antibody, 12C4, was prepared against the G5 subdomain of the laminin $\alpha$3 subunit using purified G5 recombinant protein as antigen. The preparation of this recombinant protein is described in Example 1. Induced fusion protein was purified over a $Ni^{++}$ column (Novagen, Madison, Wis.) and screened by Western blotting and Coomassie Blue staining for purity as described in Example 1. Female BALB/c mice were injected subcutaneously with the purified G5 protein. The spleen from a mouse whose serum showed reactivity against recombinant G5 protein in Western immunoblots was removed and the splenocytes were fused with SP2 mouse myeloma cells using polyethylene glycol according to standard procedures (Harlow and Lane, *Antibodies: A Laboratory Manual* (1988)). The fused cells were grown in RPMI 1640 (Sigma Chemical Co., St. Louis, Mo.) with 10% heat-inactivated fetal bovine serum (Cascade Biologics, Portland, Oreg.), HAT selection supplement (Sigma), 1 mM Na-pyruvate (Gibco BRL, Gaithersburg, Md.), 10 U/ml antibiotic/antimycotic (Gibco), and 20 mM L-glutamine (Gibco). Hybridoma cells producing G5 domain antibody were identified by Western blotting using recombinant G5 protein. Cells were cloned three times, and the cloned cells were then used to generate a high titer ascites fluid (Desmos, Inc., San Diego, Calif.).

3D5, a monoclonal antibody specific to the human laminin $\gamma$2 subunit, was generated using MCF-10A cell matrix as antigen. Briefly, female BALB/c mice were immunized with MCF-10A matrix protein preparations. Hybridoma cells were produced as above and identified by Western blotting. Cells were cloned three times, and the cloned cells used to produce a high titer ascites fluid (Desmos, Inc., San Diego, Calif).

RG13, a monoclonal antibody specific for the human laminin $\alpha$3 subunit was generated using MCF-10A cell matrix as antigen. The antibody was produced as described in the previous paragraph.

Anti-human keratin 17 antibody was the gift of Dr. Pierre A. Coulombe (Johns Hopkins University, Baltimore, Md.).

P1B5, an anti-$\alpha$3 integrin monoclonal antibody, was purchased from Gibco BRL. A rabbit polyclonal antiserum against human $\alpha$3 integrin, AB1920, was obtained from Chemicon (Temecula, Calif). A monoclonal antibody specific to the extracellular domain of human $\alpha$6 integrin, GoH3, was obtained from Immunotech (Westbrook, Me.).

D. SDS-PAGE, Western Blotting and Immunocytochemistry

Extracellular matrix preparations were generated as described in Example 1. The matrix was washed extensively with PBS, then collected in gel sample buffer consisting of 8M urea, 1% SDS in 10 mM Tris-HCl, pH 6.8, and 15% beta-mercaptoethanol. Protein samples were separated on acrylamide gels as described in Example 1 and then either stained with Coomassie Brilliant Blue or transferred to nitrocellulose membrane or to Immobilon PVDF membrane (Bio-Rad, Hercules, Calif.) by standard procedures (Harlow and Lane, *Antibodies: A Laboratory Manual* (1988)). Membranes were blocked with 5% milk in PBS, then incubated overnight at $4°$ C. with antibodies followed by the appropriate secondary antibodies. Antibody-conjugated proteins were detected with ECL chemiluminescent substrate (Amersham, Arlington Heights, Ill.).

For immunocytochemistry, cells grown on glass coverslips were either extracted for 2 minutes in $-20°$ C. acetone and then air dried, or fixed for 5 minutes in 3.7% formaldehyde in PBS. In the latter instance, cells were then extracted either in 0.5% Triton X 100 at $4°$ C. for 8 minutes when staining with integrin antibodies, or in 0.1% SDS in PBS at room temperature for 8 minutes when staining with 12C4 antibody. The fixed coverslips were subsequently placed in a damp chamber and incubated with primary antibodies at $37°$ C. for 1 hour. The coverslips were washed, incubated in the presence of the appropriate mix of fluorochrome-conjugated secondary antibodies, then mounted onto glass slides. Specimens were viewed on a LSM 410 laser-scanning confocal microscope (Zeiss Inc., Thornwood, N.Y.), digital images were captured on MO optical disks (Sony, Montvale, N.J.) and printed on a Tektronix printer (Tektronix, Wilsonville, Oreg.). Tissue specimens were prepared for immunofluorescence microscopy as detailed previously (Klatte et al., *J. Cell Biol.*, 109:3377–3390 (1989)). They were viewed and photographed with a Nikon Optiphot microscope (Nikon Inc., Melville, N.Y.).

F. Results

To confirm the specificity of the 12C4 antibody, matrix and whole cell extracts of confluent cultures of pp126 and MCF-10A cells were analyzed. As shown in the previous Examples, the matrix of pp126 cells contains primarily unprocessed $\alpha$3 subunits, while the matrix of MCF-10A cells contains primarily processed $\alpha$3 chains. See also Goldfinger et al., *J. Cell Biol.*, 141:255–265 (1998)). In addition, PCR analyses using primers for all the currently known human laminin subunits and immunochemical studies have demonstrated that laminin-5 is the major laminin isoform expressed by MCF-10A cells and that these cells do not secrete laminin-6 or laminin-7 (data not shown). The latter laminin isoforms, like laminin-5, are those that are known to contain an $\alpha$3 subunit (Champliaud et al., *J. Cell Biol.*, 132:1189–1198 (1997)).

A species of 190 kD was observed in immunoblots of pp126 extracellular matrix and whole cell extract preparations probed with 12C4 antibody. In contrast, the 12C4 antibody failed to recognize any obvious polypeptide in MCF-10A matrix although it showed reactivity with a 190 kD species in MCF-10A whole cell extracts. As a control antibody for these studies, the α3 chain monoclonal antibody 10B5, which binds both unprocessed and processed α3 subunits, was used. 10B5 antibodies recognized a 190 kD species in immunoblots of extracellular matrix and whole cell extracts derived from pp126 cells and showed reactivity with a 160 kD polypeptide in the extracellular matrix of MCF-10A cells. In addition, the 10B5 antibodies recognized a 190 kD species in MCF-10A whole cell extracts. These results confirmed data presented in the previous Examples showing that pp126 cells secrete but do not process their laminin-5 α3 subunit, whereas the α3 subunit of MCF-10A cells is converted from 190 to 160 kD following secretion. In addition, these data confirmed that the processing involves cleavage of the α3 chain within its G domain (see Example 1).

The 12C4 antibody was used to examine the location of unprocessed α3 subunit in pp126 and MCF-10A cell cultures. MCF-10A and pp126 cells grown on glass coverslips were prepared for double-label immunofluorescence using 12C4 antibodies in combination with rabbit antiserum J18 against human laminin-5. In confluent and subconfluent pp126 cultures, 12C4 and J18 antibodies colocalized in an extensive rosette-like staining pattern. J18 antibodies also stained the matrix of confluent MCF-10A cells. However, 12C4 antibodies showed little or no staining of the same preparations.

Double-label staining of subconfluent MCF-10A cell cultures with 12C4 and J18 antibodies revealed several interesting features. The J18 antibodies stained in a typical rosette-like pattern throughout the cell culture with some of the staining generated by these antibodies extending beyond the boundaries of the cells. The staining generated by 12C4 antibodies in the same preparations was not as extensive as that of the J18 serum although, where 12C4 antibodies localized, there was comparable J18 staining. Staining generated by the 12C4 antibodies in subconfluent cultures of MCF-10A cells can be divided into three distinct types of patterns. The 12C4 antibody stained the trans-Golgi network in certain cells, particularly those cells at the edges of multicell groups. This staining pattern presumably represents unprocessed and unsecreted α3 subunit. In addition, in some cells, the 12C4 antibodies showed intense staining in arc patterns located at the outer cell periphery at the edges of multicellular groups. In other cells, staining with 12C4 antibodies was often observed in arcs parallel to the cell edge, several micrometers away from the cell on the surface of the glass coverslip. Close observation revealed that the tips of long cell surface extensions of MCF-10A cells appeared to terminate in these arcs of 12C4 staining. To assess whether these extensions were filopodia or retraction fibers, images of living MCF-10A cells, maintained on "indicator" coverslips, were captured digitally every 30 minutes and, after 4 hours, the cells were processed for double-label immunofluorescence using the 12C4 and J18 antibodies. The direction of movement of at least ten cells was determined from the captured images and then the staining patterns generated in and around the same cells were assessed by immunofluorescence microscopy. The results suggested that in all instances the cell extensions that terminate close to or on the arcs of 12C4 staining are retraction fibers rather than filopodia.

The localization of integrins α6β4 and α3β1, which are receptors for laminin-5, in both pp126 and MCF-10A cell preparations (Carter et al., Cell, 65:599–610 (1991); Niessen et al., Exp. Cell Res., 211:360–367 (1994); Delwel et al., in Adhesion Receptors As Therapeutic Targets, M. A. Horton, editor, CRC Press, New York, pages 9–35 (1996)) was also examined. In pp126 cells, the staining generated by the α6 integrin antibody GoH3 was limited to small, dispersed punctate spots. Some of these spots appeared to colocalize with the laminin-5 labeled by J18 antibodies. An α3 integrin antibody stained both pp126 cell-cell contact sites as well as along the region of cell-substrate interaction. There was occasional colocalization of α3 integrin with laminin-5 staining in pp126 cells.

In subconfluent MCF-10A cell populations, although GoH3 antibodies codistributed with antigens recognized by laminin-5 antibodies in the matrix underlying cell bodies, GoH3 staining terminated just proximal to the arcs stained by 12C4 antibody. GoH3 antibody also generated a punctate staining pattern along the lengths of retraction fibers, although GoH3 antibodies did not stain the tips of the fibers where there was a concentration of 12C4 antigen. The retraction fibers in these cells also contained α3 integrin, although α6 and α3 integrins did not appear to co-localize. In general, the α3 integrin antibody appeared to stain the retraction fiber tips, whereas α6 integrin antibodies did not. In addition, antibodies against α3 integrin showed some colocalization with 12C4 antibodies in certain of the arc-like patterns that occurred toward the edge of subconfluent MCF-10A cells. However, there were many instances where 12C4 staining patterns and α3 integrin localization were distinct. For example, α3 integrin was commonly found at sites of MCF-10A cell-cell contact whereas 12C4 staining was not.

The fate of the unprocessed α3 laminin subunit in matrix of migrating MCF-10A cells was also followed as the cells covered a scrape wound. For these studies, confluent cultures of MCF-10A cells on coverslips were wounded by a single pass with a plastic pipette tip. The wounded cultures were allowed to heal for 6, 12, 18 or 24 hours before being fixed and labeled with 12C4 antibodies. Scrape wounds were completely healed by 18 hours, with the cells moving as a sheet over the denuded cell culture substrate. Expression of unprocessed α3 laminin subunit was upregulated at the wound edges, as evidenced by intense Golgi staining in most cells along the wound edge by 12C4 antibodies. The latter also strongly stained the leading edges of those cells that were migrating into the wound space. This was true at all stages of wound healing prior to wound closure. Consistent with these data, 12C4 antibodies recognized a 190 kD polypeptide in immunoblots of matrix preparations derived from MCF-10A cell cultures that had been wounded and allowed to undergo partial healing for 8 hours. 12C4 antibodies did not recognize any species in matrix preparations derived from confluent, non-wounded MCF-10A cell cultures. It should also be noted that 12C4 recognized a group of polypeptides in the molecular weight range 21 to 39 kD in matrix derived from wounded cultures. These low molecular weight species may represent cleaved fragments of the α3 chain. In addition, although it has been reported that the γ2 chain of laminin-5 is cleaved by MMP-2 resulting in the production of a 80 kD fragment during tissue remodeling, no evidence was found of such a fragment in the γ2 chain of laminin-5 in the matrix of MCF-10A cell cultures that have been wounded and allowed to heal (Giannelli et al., Science, 277:225–228 (1997)).

Whereas α6 integrin was polarized basally in unwounded, confluent cultures of MCF-10A cells, in migrating MCF-10A cells which reepithelialized in vitro wounds, α6 integrin was found both at cell-cell contact sites and along sites of cell-substrate interaction. This is consistent with localization data presented by Kurpakus et al., *J. Cell Biol.*, 115:1737–1750 (1991) who analyzed the organization of α6β4 integrin in the migrating epithelium of a tissue explant wound healing model. However, α6 integrin was not found co-distributed with unprocessed α3 laminin subunit. On the other hand, α3 integrin, which was found predominantly at regions of cell-cell interaction, was occasionally found colocalized with unprocessed α3 laminin subunit at the leading front of cells migrating over the wound site.

Wounded MCF-10A cultures were processed 8 hours post-wounding for electron microscopy (see Example 3). Neither mature nor immature hemidesmosomes were observed in those cells at the leading front of the migrating epithelial sheet. In contrast, MCF-10A cells populating scrape wounds possessed some hemidesmosome-like structures. These appeared immature compared with hemidesmosomes in cells in unwounded cultures.

The immunofluorescence results indicated a role for the α3 laminin subunit and one of its cell surface receptors (α3β1 integrin) in epithelial wound healing. To investigate this further, the impact was assessed of antibodies RG13 and P1B5, as well as GoH3, which inhibit the function of α3 laminin subunit, α3 integrin and α6 integrin respectively, on wound healing (Sonnenberg et al., *Nature*, 336:487–489 (1988); Carter et al., *Cell*, 65:599–610 (1991); Gonzales et al., Laminin-5 and its role in the proliferation of epithelial cells, in press, *Mol. Biol. Cell*). In brief, scrape wounds were introduced into confluent MCF-10A cell cultures and then allowed to heal for 18 hours in the presence of the appropriate antibody. Wounds in cell populations incubated without antibody or in irrelevant antibody healed completely within the experimental time frame. When α6 integrin-blocking antibody GoH3 was added to the wounded cultures, healing was partially inhibited, with approximately 70% wound closure in 18 hours. Wound healing was blocked to a markedly greater degree (41.6% closure) in the presence of α3 integrin-blocking antibody P1B5. When antibodies to both α3 and α6 integrins were combined, wound healing was almost completely inhibited (9.5% closure). Wound healing was also completely blocked (3.2% closure) when the wounded cultures were incubated in the presence of RG13, a function-blocking antibody that recognizes the G domain of the α3 laminin subunit.

Since the combination of GoH3 and P1B5 antibodies was more efficient than the same antibodies used singly in inhibiting MCF-10A cell culture wound healing, this raised the possibility that α6β4 and α3β1 integrins may overlap in some of their functions. To investigate this further, the localization of α3 integrin in GoH3-antibody treated, motile MCF-10A cells located away from the leading front of migrating cells was analyzed. The α3 integrin subunit was predominantly at cell-cell contact points with little, if any, α3 integrin being localized at sites of cell-substrate interaction in unwounded confluent MCF-10A cell populations. In sharp contrast, in cells in wounded, GoH3 antibody-treated cultures, α3 integrin was present both at cell-cell contacts as well as at the basal cell surface.

To determine whether the expression of unprocessed laminin-5 α3 subunit was observed during wound healing in vivo, sections of normal and wounded, healing human skin were prepared. A monoclonal antibody that recognizes the human laminin γ2 subunit, GB3, stained throughout the basement membrane in normal, unwounded skin and in skin 2 days post-wounding. In contrast, 12C4 antibodies failed to recognize the basement membrane of the epidermis in normal skin sections, but stained the basement membrane of epidermal cells repopulating a wound. These same cells were stained by an antiserum against keratin 17 (K17) which has been shown to be present at high levels in keratinocytes migrating to cover a wound (Paladini et al., *J. Cell Biol.*, 132:381–397 (1996)).

These studies show that unprocessed laminin α3 subunit has a distinctive distribution in cultured cells. In pp126 cells, which fail to process their α3 subunit to any obvious degree, the monoclonal antibody 12C4 stained throughout the matrix of the cells. In contrast, no unprocessed α3 subunit is seen in the laminin-5-rich matrix of confluent MCF-10A cells. However, unprocessed α3 subunit can be detected in the matrix of certain cells in subconfluent MCF-10A cell cultures. In particular, the unprocessed α3 subunit often appears to be organized into circles or arcs toward the "free" outer edges of those MCF-10A cells in small multicellular groupings. Unprocessed α3 subunit has also been observed in the same arc pattern outside the boundary of the MCF-10A cells. MCF-10A cells deposit a matrix, containing unprocessed α3 subunit, toward their outermost edges. Provided the cell moves over the newly deposited laminin, then the α3 subunit is processed.

Unprocessed α3 subunit was also detected in the matrix beneath the first layer of cells of the MCF-10A multicellular sheet which repopulates in vitro scrape wounds. The uncleaved α3 subunit is restricted to this site. The same is true in healing wounds of the epidermis, i.e. unprocessed α3 laminin subunit is found in the matrix of the leading tip of epidermal cells populating an in vivo wound. It is supposed that as the sheet of cells moves over the wound bed, both in vitro and in vivo, the unprocessed α3 subunit is rapidly cleaved such that the majority of cells in the migrating cell population lie on a laminin-5-rich matrix containing processed α3 subunit.

Using a laminin-5 α3 subunit function-perturbing antibody and MCF-10A cells, direct evidence for an important functional role for the α3 chain of laminin-5 in the process of wound closure has been provided, i.e. antibody RG13 inhibits closure of scrape wounds made in MCF-10A cultures. Since RG13 appears to impede the initiation of migration of cells from the wound edge over the wound bed, it is presumed that RG13 has a direct, inhibitory impact on laminin heterotrimers containing unprocessed α3 subunit, which are deposited at the very leading edge of the sheet of migrating epithelial cells. Indeed, since this particular form of laminin-5 is a motility factor for cells (see previous Examples), the results indicate that the laminin-5 containing unprocessed α3 subunit drives the forward motion of the sheet of migrating cells which covers a wound site. Since it is highly improbable that the leading front of cells can drag the more distal cells in the sheet over the wound site, it is suggested that laminin-5 containing unprocessed α3 subunit is more likely to initiate a cell-cell signaling cascade which regulates the spreading and migration of the distally located cells.

One intriguing aspect of the results is that processed α3 subunit occurs in the matrix of the cells within the actively migrating cellular sheet which covers the MCF-10A scrape wounds as well as in the matrix of the epidermal cells populating in vivo wounds. It has been shown that cells maintained on laminin-5 containing processed α3 subunit show reduced migration (see previous Examples; O'Toole et al., *Exp. Cell Res.*, 233: 330–339 (1997); Goldfinger et al., *J. Cell Biol.*, 141:255–265 (1998)). One might assume, therefore, that this particular matrix would impede epithelialization of the wound. However, wounds in MCF-10A cell cultures and in vivo clearly heal despite the presence of processed α3 subunit in the matrix of the migrating epithelial cell sheet. The presence of two functionally distinct α3 laminin subunits in the matrix of the migrating cells reflects the somewhat conflicting processes that occur during wound healing. One of these processes leads to the migration of cells to ensure that a wound site is covered. At the same time there must be stabilization of epithelial cell-wound bed interaction (Garlick et al., *Lab. Invest.*, 70:916–924 (1994); Martin, *Science*, 276:75–81 (1997)). Because it can function both as a motility factor and as an adhesive substrate depending on its subunit makeup, laminin-5 is ideally suited to function in both events and appears to play a key role in the balance between these two processes. In other words, at the leading edge of the sheet of cells that populate a wound, laminin-5 appears to facilitate cell migration. In contrast, in more distal regions of the migrating cellular sheet, laminin-5 appears to play a role in stabilizing cell-substrate interaction. It may do so by ligating $\alpha 6\beta 4$ integrin, which is localized along the site of cell-matrix interaction in the migrating epithelial cells. It is speculated that formation of such a laminin-5/$\alpha 6$ $\beta 4$ complex leads to the assembly of mostly immature hemidesmosomes, as described at the ultrastructural level. These may be more dynamic than their mature counterparts, allowing cell migration to occur while also providing stability to cell-wound bed interaction.

The immunofluorescence analyses revealed that $\alpha 3$ integrin colocalizes in some instances with matrix containing the unprocessed laminin $\alpha 3$ subunit both in pp126 and MCF-10A cells. This suggests the possibility that $\alpha 3\beta 1$ integrin may be involved in transducing the motility "signal" of the unprocessed $\alpha 3$ laminin subunit. Experimental support for this speculation is provided since the $\alpha 3$ integrin antibody P1B5 inhibits closure of MCF-10A cell scrape wounds. However, P1B5 antibodies inhibit wound closure less efficiently than the $\alpha 3$ laminin subunit antibody RG13 implying that another integrin or non-integrin matrix receptor may be involved in the wound healing process. This integrin appears to be $\alpha 6\beta 4$ integrin since a combination of P1B5 antibody and the $\alpha 6$ integrin antibody GoH3 inhibits closure of MCF-10A cell wounds almost as well as the $\alpha 3$ laminin subunit antibody. Perhaps the GoH3 antibody prevents the assembly of the type II-like hemidesmosomes mentioned above. This may perturb adherence of the migrating epithelial cells to the wound surface thereby inhibiting wound closure.

The results also suggest that the roles of $\alpha 3\beta 1$ and $\alpha 6\beta 4$ may be somewhat interchangeable or overlapping (Xia et al., *J. Cell Biol.*, 132:727–740 (1996)). In other words, when the function of the $\alpha 3$ integrin subunit is inhibited in wounded cultures of MCF-10A cells, $\alpha 6\beta 4$ integrin may be capable of partially mediating signals which lead to cell motility. This could occur directly, via a $\alpha 6\beta 4$ integrin association with the microfilament network of epithelial cells, or indirectly, by some sort of "cross-talk" with another integrin heterodimer. In addition, when the function of $\alpha 6$ integrin is inhibited, the $\alpha 3\beta 1$ integrin heterodimer may help stabilize cell attachment to the matrix in the wound bed. Evidence for this is provided since, in $\alpha 6$ integrin antibody-treated wounded MCF-10A cell cultures, $\alpha 3$ integrin is found along sites of cell-substrate interaction in migrating MCF-10A cells, where it may substitute for $\alpha 6\beta 4$ integrin in maintaining cell-wound bed interaction. This would explain why blocking the function of both $\alpha 3$ and $\alpha 6$ integrins almost completely inhibits migration and closure of a MCF-10A cell scrape wound.

Based on the results presented here, the following model to explain the role of laminin-5 and its integrin receptors in epithelial wound healing is proposed. In this model, in a "resting" stratified epithelial tissue, laminin-5, containing processed $\alpha 3$ subunit, binds to $\alpha 6$ $\beta 4$ integrin in hemidesmosomes in basal epithelial cells, while $\alpha 3\beta 1$ integrin is localized to the lateral cell surfaces. Upon wounding, production of laminin-5 is upregulated and/or there is a concomitant down-regulation of laminin-5 $\alpha 3$ subunit processing at the wound edge. This results in deposition of unprocessed $\alpha 3$ laminin subunit at the leading edge of the wound. The integrin $\alpha 3\beta 1$ interacts with the unprocessed $\alpha 3$ laminin subunit in a way that encourages cell migration over the wound bed. In the same cells, $\alpha 6\beta 4$ integrin concentrates at the lateral cell surfaces. In contrast, in cells some distance away from the leading tip of epithelium, $\alpha 6\beta 4$ integrin locates not only at sites of cell-cell contact but also along the basal surface of the cells where it can bind matrix containing processed $\alpha 3$ subunit. The latter interaction stabilizes the attachment of the migrating sheet of cells to the wound bed.

We claim:

1. A method of generating hemidesmosome-promoting laminin-5 comprising:

culturing epithelial cells that do not produce hemidesmosome-promoting laminin-5 under conditions effective so that they produce extracellular matrix protein comprising laminin-5 containing unprocessed $\alpha 3$ subunits; and contacting the laminin-5 with plasmin under conditions effective so that the plasmin cleaves the $\alpha 3$ subunits.

2. The method of claim 1 wherein the plasmin is generated by contacting plasminogen with a plasminogen activator.

3. The method of claim 2 wherein the plasminogen activator is a tissue-type plasminogen activator.

4. The method of claim 2 wherein the extracellular matrix protein is contacted with the plasminogen and then with the plasminogen activator.

5. The method of claim 1 wherein the laminin-5 is human laminin-5.

6. The method of claim 1 wherein the laminin-5 is isolated from the extracellular matrix protein prior to being contacted with the plasmin.

7. A method of generating hemidesmosome-promoting laminin-5 comprising:

producing heterotrimeric laminin-5 containing unprocessed $\alpha 3$ subunits by expressing DNA coding for $\alpha 3$, $\gamma 2$ and $\beta 3$ subunits in host cells transformed with the DNA; and contacting the laminin-5 with plasmin under conditions effective so that the plasmin cleaves the $\alpha 3$ subunits.

8. The method of claim 7 wherein the $\alpha 3$, $\gamma 2$ and $\beta 3$ subunits are produced in the same host cell.

9. The method of claim 7 wherein the $\alpha 3$, $\gamma 2$ and $\beta 3$ subunits are produced in different host cells.

10. The method of claim 7 wherein the laminin-5 is isolated prior to being contacted with the plasmin.

11. The method of claim 7 wherein the laminin-5 is human laminin-5.

12. A method of generating hemidesmosome-promoting laminin-5 comprising:

contacting a material containing unprocessed $\alpha 3$ subunits of laminin-5, but not $\gamma 2$ subunits or $\beta 3$ subunits of laminin-5, with plasmin under conditions effective so that the plasmin cleaves the $\alpha 3$ subunits; and contacting the cleaved $\alpha 3$ subunits with $\gamma 2$ and $\beta 3$ subunits so that the three subunits combine to form the hemidesmosome-promoting laminin-5.

13. The method of claim 12 wherein the laminin-5 is human laminin-5.

14. The method of claim 1, 7 or 12 further comprising applying the hemidesmosome-promoting laminin-5 to a shaped article.

\* \* \* \* \*